US00PP12302P2

(12) United States Plant Patent
Clark et al.

(10) Patent No.: US PP12,302 P2
(45) Date of Patent: Dec. 25, 2001

(54) GRAPEVINE-NEPTUNE CULTIVAR

(75) Inventors: John Reuben Clark; James Norman Moore, both of Fayetteville, AR (US)

(73) Assignee: University of Arkansas, Fayetteville, AR (US)

( * ) Notice: Subject to any disclaimer, the term of this patent is extended or adjusted under 35 U.S.C. 154(b) by 0 days.

(21) Appl. No.: 09/250,920

(22) Filed: Feb. 16, 1999

(51) Int. Cl.[7] ..... A01H 5/00
(52) U.S. Cl. ..... Plt./207
(58) Field of Search ..... Plt./207

(56) References Cited
PUBLICATIONS
http://www.geog.ucsb.edu/~jeff/115a/younghemltheory.html#chap3, Aug. 2000.*
* cited by examiner

*Primary Examiner*—Bruce R. Campell
*Assistant Examiner*—Anne Marie Grünberg

(57) ABSTRACT

Description and specifications of a new and distinct grapevine variety which originated from a hand-pollinated cross of Arkansas Selection 1562 (non-patented) and Arkansas Selection 1704 (non patented) are provided. This new grapevine variety can be distinguished by its attractive yellow-green seedless fruit, excellent sweet fruity flavor, resistance to fruit cracking, and large attractive clusters.

2 Drawing Sheets

SUMMARY OF THE INVENTION

Figure 1:
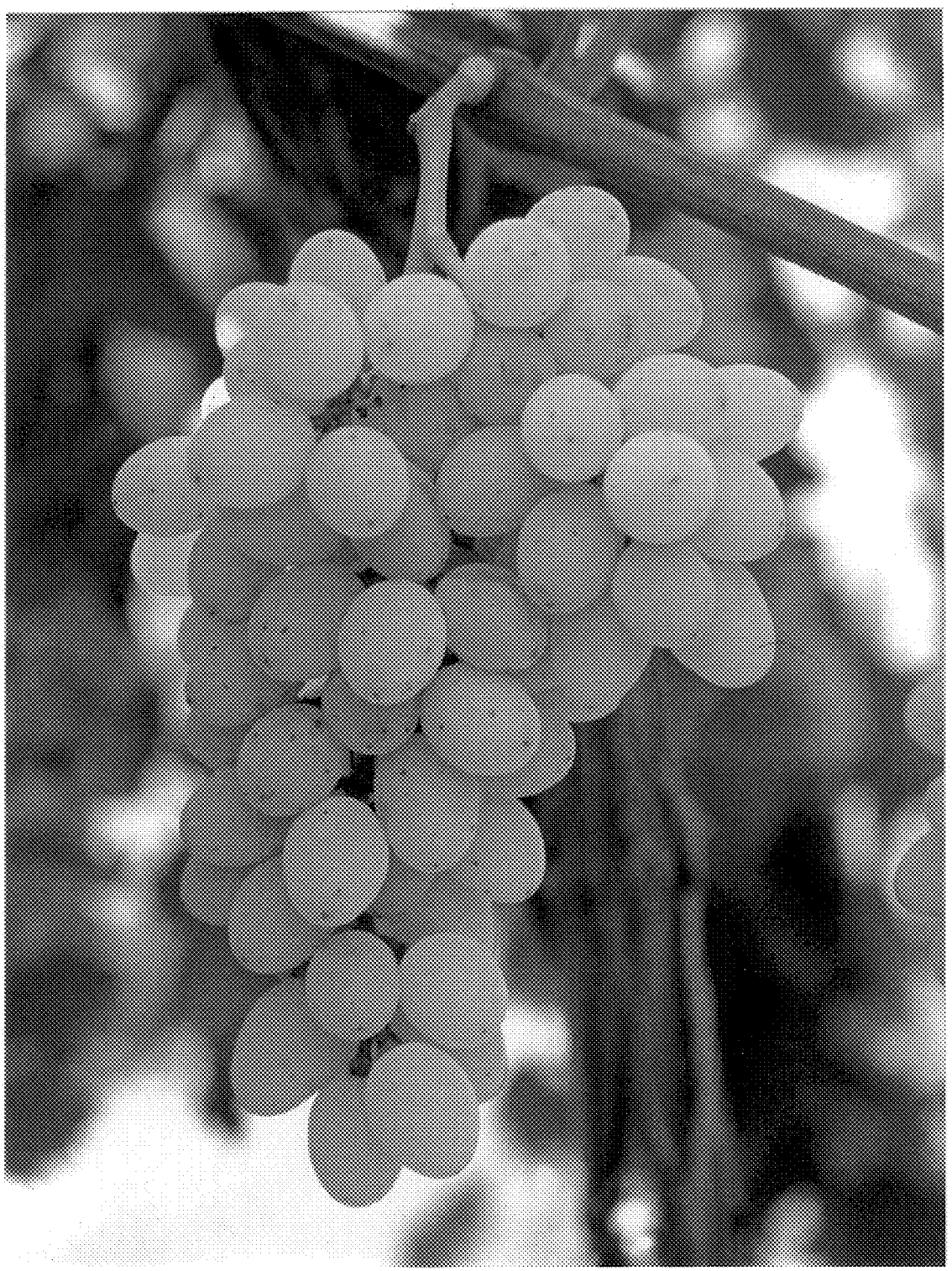

The new and distinct variety of grapevine originated from a hand-pollinated cross of Arkansas Selection 1562 (non-patented)×Arkansas Selection 1704 (non-patented) made in 1985 at the Arkansas Agricultural Experiment Station Fruit Substation at Clarksville, Ark. Arkansas Selection 1562 is a seeded, blue-fruited grape with very large, narrow elliptic, non-slipskin (pulp adheres to the flesh) berries with a fruity flavor that ripen near the same date as the instant variety. Arkansas Selection 1704 is a seedless, green or white-fruited grape with medium, oblong and pointed, non-slipskin (pulp adheres to the flesh) berries, that ripen near the same date as the instant variety. Both of the parents of the instant cultivar are hybrids of the grape genus and species *Vitis labrusca* L. and *Vitis vinfera* L. Thus the instant cultivar is also of this two-species genetic background. The seeds resulting from this controlled hybridization were germinated in a greenhouse during the winter of 1985–86. Resulting seedlings were planted in the spring of 1986 in a vineyard on the Arkansas Agricultural Experiment Station at Clarksville, Ark. The seedlings fruited in the summer of 1988 and one, designated Arkansas 2083, was selected for its attractive yellow-green seedless fruits, fruity flavor, and resistance to fruit cracking.

During 1988, the original plant selection was propagated asexually by rooting hardwood cuttings at Clarksville, Ark. and a test planting of three vines was established. Subsequently, larger test plantings have been established with asexually multiplied vines at two additional locations in Arkansas (Fayetteville, Ark. and Searcy, Ark.). In all propagations, hardwood cuttings were used and the instant cultivar roots readily from hardwood cuttings. All propagules (resulting plants) of the instant cultivar have been observed to be true to type in that during all asexual multiplication, the vegetative and fruit characteristics of the original plant have been maintained. All vines planted from hardwood cutting propagation fruited in the third season of growth in the vineyard after planting.

Test plantings over a wide geographic area in Arkansas have shown this new variety to be widely adapted to differing soil and climatic conditions. It has shown moderate winter hardiness during cold winters, having similar hardiness to the cultivar 'Venus' (non-patented), but being less hardy than the cultivars 'Mars' (U.S. Plant Pat. No. 5,680) and 'Reliance' (U.S. Plant Pat. No. 5,174). Canes of the new variety mature in the fall at similar time to the cultivar 'Venus' but not as early as the cultivar 'Mars'.

Vines of the new variety have medium to semi-low vigor and a semi-upright growth habit. Vigor, as reflected in dormant pruning weights measured on mature vines, indicated that the instant cultivar was less vigorous than 'Mars' and 'Venus'. Also, vine size as determined on vines growing on a Four-Arm Kniffin trellis with the top wire of this trellis placed at a height of 4 ft. 10 in., indicated a vine height of 6 ft. 2 in. and a vine spread of 3 ft. 0 in. It has produced well as own-rooted plants in all locations tested.

The new variety is moderately resistant to most common fungus diseases of grapevines. Under normal chemical disease control programs, the vines and fruit have demonstrated good freedom from black rot (*Guignardia bidwellii* (Ell.) V. & R.), anthrancnose (*Elsinoe ampelina* (d. By.) Sher), and powdery mildew (*Uncinula necator* Burr.). Susceptibility to downy mildew (*Plasmopora viticola* Berl. & Tomi.) is similar to that of 'Venus', and is controllable by the use of available fungicides. The fruit has shown no inclination to split following rains, or powdery mildew infections.

The new variety ripens its fruit in midseason, 16 days later than the early maturing 'Venus' cultivar, six days later than 'Reliance', and one day earlier than 'Mars'. The average ripening date in August 4 in central Arkansas. The fruit quality is maintained well on the vine after maturity. Fruit of sound quality for marketing is maintained for up to four weeks on the vines after initial maturity is reached. Berries adhere well to the fruit pedicel and do not shatter from the clusters during this time.

The fruit yellow-green in color at maturity. It is evenly colored with the cluster. The fruit shape is elliptic to slightly ovate. Fruit skins are moderately thick and thinner that those of 'Venus'. Pulp adheres to the skins of the berry and texture is highly rated. The berries are medium in size (ca. 2.5 g), being larger than 'Reliance', similar to 'Mars', and smaller than 'Venus'. The flavor is fruity and sweet, and has been consistently rated high. Soluble solids concentration of the juice at fruit maturity average 19.7% with pH of 3.2. The fruit is of the stenospermocarpic type of seedlessness and only rarely contains small, soft vestigial seed traces that are not noticeable when eaten.

Fruit clusters, borne usually two per shoot, are conical and often have a small shoulder. They are large in size (ca. 345 g), well-filled, and very attractive. Fruit cluster peduncles are medium-long and easy to remove from the supporting shoots during harvest.

The new variety has been named the 'NEPTUNE' cultivar.

BRIEF DESCRIPTION OF THE PHOTOGRAPHS

Figure 2:
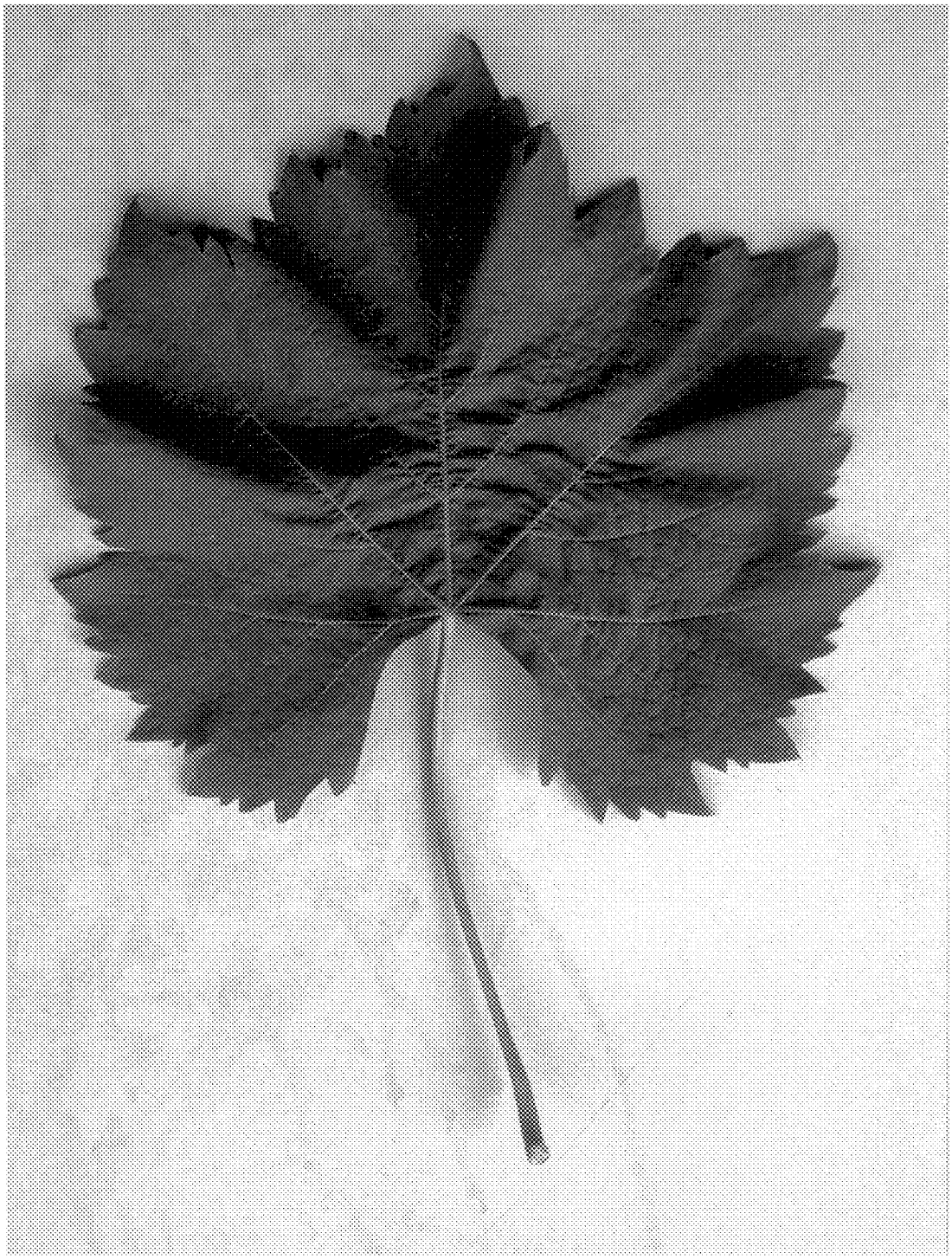

The accompanying photographs show typical specimens of the fruit (FIG. 1) and leaf (FIG. 2) of the new variety in color as nearly true as it is reasonably possible to make in a color illustration of this character.

DETAILED DESCRIPTION OF THE NEW VARIETY

The following is a detailed description of the botanical and pomological characteristics of the subject grapevine. Color data are presented in Royal Horticultural Society Colour Chart designations and are supplemented with readings from a Minolta Chroma Meter CR-200, version 3.0, which measures absolute chromaticity in tristimulus values Y, x, and y. Calibration was performed using a standard white plate supplied by the manufacturer.

Where dimensions, sizes, colors and other characteristics are given, it is to be understood that such characteristics are approximations of averages set forth as accurately as practicable.

The descriptions reported herein are from specimens grown at Clarksville, Ark. unless otherwise noted. Vines used for measurement were grown on a Linker fine sand loam soil and the vines were irrigated using trickle (drip) irrigation. The majority of the data collection was from vines that were 9 years old.

Vine:

*Size.*—Medium-large; vine size as determined on vines growing on a Four-Arm Kniffin trellis with the top wire of this trellis placed at a height of 4 ft. 10 in., indicated a vine height of 6 ft. 2 in. and a vine spread of 3 ft. 0 in.

*Growth.*—Medium to semi-low vigor; comparative vigor as measured by weighing prunings at dormant pruning with pruning severity to a standard formula of 30 +10 (thirty buds left on the vine for the first one pound of prunings and 10 buds left for each subsequent pound of prunings) indicated a pruning weight of 'Neptune' of 1.3 lb, 'Mars' 4.1 lb, and 'Venus' 1.8 lb. Bud break March 25.

*Productivity.*—Medium, 6 t/acre on vines spaced 8 ft.×10 ft.;similar to 'Venus' and 'Mars'.

*Cold hardiness.*—Hardy to −17° C.

*Canes.*—Medium diameter, semi-upright in growth habit. Diameter of mature cane: base 1.31 cm, midpoint 0.58 cm, terminal 0.15 cm. Internode length: base 4.52 cm, midpoint 8.15 cm, terminal 3.05 cm. Color of mature cane: base Greyed-Orange Group (165A); midpoint Greyed Orange Group (165B); terminal Greyed-Orange Group (165B); no anthocyanin observed on mature canes; lenticels present on mature canes and are numerous, scattered and small (less than 0.5 mm in diameter). Annual pruning of canes is required for reliable production. Diameter of young shoots in spring (measured when shoots are 6–12"): base 0.7 cm, midpoint 0.5 cm, terminal 0.2 cm. Internode length 4.33 cm. Shoot tips have no anthocyanin present.

*Tendrils.*—Total length averages 25 cm (total length including all forked sections); texture smooth; usually double-forked and curled on distal end. Color of mature tendril is Greyed-Orange Group (175A). Tendrils found beginning opposite node 5 then again at nodes 6, 8, 9, 11,12 with this repeating intermittent pattern to the distal end of the cane.

*Buds.*—Average number of buds on a current, single-season growth cane is 30; dormant bud (compound bud or eye) width 6.0 mm; shape triangular; color Greyed-Orange Group (165A); texture smooth.

*Disease resistance.*—Moderate resistance to fungus diseases black rot, powdery mildew, and anthracnose; moderately susceptible to downy mildew.

*Insect resistance.*—Insecticides were applied to the vines under evaluation to control climbing cutworms, grape berry moth and green June beetle. No resistances to these pests were determined in these evaluations due to chemical control of these pests.

Foliage:

*Leaves.*—Leaves simple and alternate; shape ovate to suborbicular; number of lobes 3; petiole sinus shape half open; venation palmate-pinnate; margin serrated with shape of teeth rectalinear and teeth short to medium in size. Color of mature leaves: base abaxial-Green Group (138B) Y=17.96, x=0.3483, y=0.4168; adaxial-Green Group (137B) Y=10.24, x=0.3395, y=0.4158; midpoint abaxial-Green Group (138B) Y=17.76, x=0.3483, y=0.4173; adaxial-Green Group (137C) Y=10.34, x=0.3438, y=0.4202; terminal abaxial-Green Group (138B) Y=17.56, x=0.3465, y=0.4139; adaxial-Green Group (137B) Y=9.97, x=0.3385, y=0.4113. Color of petioles Green Group (142B). Very slight anthocyanin present on entire surface of petioles on young leaves with decreasing anthocyanin intensity as leaves age, with anthocyanin near absent on oldest leaf petioles. Leaf petiole length is 10.02 cm. Sinus of mature leaf is 4.53 cm deep and 2.23 cm at widest point. No anthocyanin on upper or lower surfaces of leaves or on leaf veins. Mature leaves are glabrous on the abaxial surface; pubescence on the adaxial surface is of very light density and irregular in distribution, prostrate, and present only on veins on the adaxial surface. Light, prostrate pubescence is found on the adaxial surface of newly-emerged leaf petioles with glabrous petioles on fully-expanded leaves. Color of young (unfolded) leaves: base abaxial Yellow-Green Group (146B) Y=17.32, x=0.3521, y=0.3748; adaxial Yellow-Green Group (148A) Y=11.92, x=0.3742, y=0.4020; midpoint abaxial-Yellow-Green Group (146B) Y=15.98, x=0.3571, y=0.3880; adaxial-Yellow-Green Group (148A) Y=11.28, x=0.3715, y=0.3971; terminal abaxial Yellow-Green Group (146B) Y=16.22, x=0.3538, y=0.3794; adaxial-Yellow-Green Group (146A) Y=11.59, x=0.3754, y=0.3965. Petiole color of young leaves Yellow-Green Group (146C).

Flowers:(as measured at the time of full bloom/anthesis):

*Inflorescence*.—Panicle.

*Date of bloom*.—First: May 12; Last: May 25.

*Stamen color*.—Filament: White group (155A); Anther freshly opened greyed-yellow group (162C).

*Stamen number*.—5.

*Pistil number*.—1.

*Pistil length*.—3.0 mm.

*Pistil color*.—Yellow-green group (144B).

*Petal number*.—5, fused in a calyptra.

*Petal color*.—Yellow-green group (144B).

*Petal shape*.—Cohering at the summit, separating at the base; 3 mm long, 1 mm wide at fused end; separated end reflexed after dehiscence from flower.

*Sepal number*.—5, flat round without lobes.

*Sepal color*.—Yellow-green group (144B).

*Pollen color*.—Greyed-yellow group (162D).

*Individual entire flower dimensions*.—3.1 mm length, 1.3 mm width.

*Number of flowers per cluster*.—425.

*Flower fragrance*.—Yes.

*Shape of cluster*.—Conical, with occasional small shoulder.

*Size of cluster*.—Length: 12.8 to 15.9 cm; $\bar{x}$=13.9 cm. Width: 9.8 to 11.9 cm; $\bar{x}$=10.7 cm.

Fruit:

*Maturity*.—Midseason, sixteen days after 'Venus'. Average ripe date is August 4. Even ripening in cluster.

*Size*.—Medium, avg. 2.5 g, uniform in size.

*Shape*.—Elliptic to slightly ovate, uniform.

*Color*.—Yellow-Green at maturity, Yellow Green Group (145A).

*Texture*.—Semi-crisp.

*Skin*.—Moderately thick, adhering to flesh (non-slipskin), semi-crisp.

*Character of seeds*.—Stenospermocarpic seedless, small vestigial seeds rarely present and not lignified and unnoticeable when eaten.

*Brush length*.—4.7 mm.

*Peduncle length*.—10.0 cm.

*Flavor*.—Fruity, sweet.

*Soluble solids*.—19.7%.

*pH*.—3.2.

*Mature cluster weight*.—345 g.

*Mature cluster size*.—Length 20 cm; width 16.5 cm.

*Pedicel*.—Length 5 mm; diameter 2 mm; color green; texture semi-smooth with abundant lenticels; arrangement of 3 to 5 berries with pedicels arising from a single point of origin from the secondary branch from the rachis.

*Berries per cluster*.—77–150, $\bar{x}$=101.

*Cluster per vine*.—40–73, $\bar{x}$=48.

*Clusters per shoot*.—Usually 2.

*Uses*.—Fresh consumption when seedlessness and fruity flavor is desirable in a yellow-green grape. No wine nor raisin evaluations have been done on 'Neptune'.

The variety: The most distintive features of the variety are its attractive, yellow-green seedless berries, excellent sweet fruity flavor, resistance to fruit cracking, and large attractive clusters.

We claim:

1. A new and distinct variety of grape plant, substantially as illustrated and described, characterized by its attractive yellow-green seedless berries, excellent sweet fruity flavor, resistance to fruit cracking, and large attractive clusters.

* * * * *